(12) United States Patent
Doty

(10) Patent No.: US 8,054,985 B2
(45) Date of Patent: Nov. 8, 2011

(54) LOW SOUND ATTENUATING HEARING PROTECTION DEVICE WITH FILTER ARRANGEMENT

(75) Inventor: Marc L. Doty, Brownsburg, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 720 days.

(21) Appl. No.: 11/704,475

(22) Filed: Feb. 9, 2007

(65) Prior Publication Data

US 2007/0183606 A1     Aug. 9, 2007

Related U.S. Application Data

(63) Continuation-in-part of application No. 10/700,213, filed on Nov. 3, 2003, now Pat. No. 7,697,706.

(51) Int. Cl.
*A61F 11/06* (2006.01)
*H04R 25/00* (2006.01)

(52) U.S. Cl. ............................. 381/72; 381/322; 381/328

(58) Field of Classification Search .................... 381/72, 381/328, 312, 322, 380; 128/864; 181/129, 181/130, 135
See application file for complete search history.

(56) References Cited

U.S. PATENT DOCUMENTS

| | | | | |
|---|---|---|---|---|
| 3,080,011 A * | 3/1963 | Henderson | ..................... | 181/135 |
| 3,131,241 A | 4/1964 | Mendelson | | |
| 4,461,290 A * | 7/1984 | Gardner et al. | ................ | 128/866 |
| 5,113,967 A * | 5/1992 | Killion et al. | .................. | 181/132 |
| 5,936,208 A | 8/1999 | Hamery | | |
| 6,938,622 B2 * | 9/2005 | Huang | .......................... | 128/864 |
| 7,162,039 B1 * | 1/2007 | Callahan | .......................... | 381/67 |
| 2003/0081805 A1 * | 5/2003 | Fushimi | ........................ | 381/325 |

FOREIGN PATENT DOCUMENTS

| | | |
|---|---|---|
| CN | 2249070 | 3/1997 |
| EP | 0955025 | 11/1999 |
| EP | 1046382 A1 | 10/2000 |
| TW | 92129573 | * 10/2003 |
| WO | 9718779 | 5/1997 |
| WO | 0176520 | 10/2001 |
| WO | 2005041830 | 5/2005 |

OTHER PUBLICATIONS

International Search Report PCT/US2008/001607; Dated Sep. 3, 2008.

* cited by examiner

*Primary Examiner* — Devona Faulk
*Assistant Examiner* — George Monikang
(74) *Attorney, Agent, or Firm* — Karl G. Hanson

(57) ABSTRACT

A hearing protection device including a sound attenuating portion configured to be disposed within an ear canal of a user to obstruct a passage of sound, a channel formed through the sound attenuating portion configured to allow sound to pass through the sound attenuating portion when the portion is disposed within the ear canal, a tube disposed in the channel and configured to allow the sound in the channel to pass therethrough, and a filter disposed at one end of the tube and positioned at an interior of the sound attenuating portion, where the filter attenuates some of the sound passing through the tube.

18 Claims, 12 Drawing Sheets

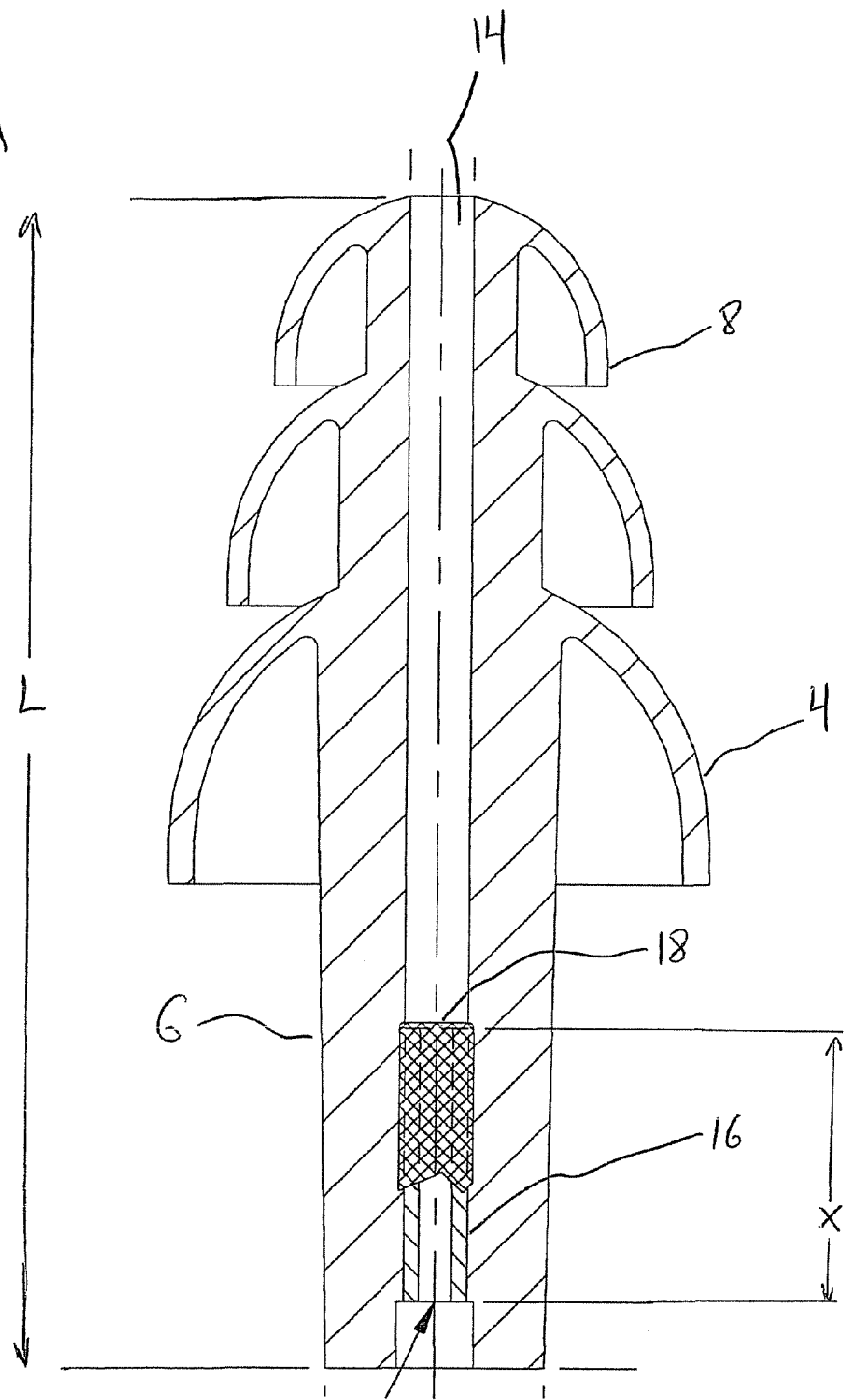

LOW SOUND ATTENUATING HEARING PROTECTION DEVICE WITH FILTER ARRANGEMENT

CROSS REFERENCE TO RELATED APPLICATION

This application is a continuation-in-part of U.S. patent application Ser. No. 10/700,213 filed on 3 Nov. 2003 now U.S. Pat. No. 7,697,706, the contents of which are herein incorporated by reference in their entirety.

TECHNICAL FIELD OF INVENTION

The invention concerns hearing protection devices and, more particularly, hearing protection devices which provide a low or relatively reduced sound attenuation.

DESCRIPTION OF RELATED ART

Hearing protection devices, such as earplugs and semi-aural devices, are readily used to provide sound attenuation. Such devices are inserted into the ear canal of a user, or placed over the opening of the ear canal, to physically obstruct the passage of sound waves into the inner ear.

Earplugs include any of a variety of devices designed to be inserted in the ear canal of a user and worn therein to prevent sounds from entering. Push-in type earplugs comprise an attenuating portion and a rigid or semi-rigid portion typically extending therefrom or embedded therein. The sound attenuating portion may be a rubber, plastic, or foam material; the rigid or semi-rigid portion may be composed of any material, such as a plastic or a rubber, with sufficient rigidity as required. To insert the push-in type earplug, the user grasps the rigid/semi-rigid portion (or an end of the earplug proximate thereto), positions the earplug proximate the ear canal opening, and inserts the sound attenuating portion into the canal by pushing with the rigid/semi-rigid portion. The sound attenuating portion compresses, as necessary, upon entry into the ear canal and is held therein by a friction fit occluding the canal and thus attenuating sound.

Such a push-in type earplug may be found, for example, in U.S. Pat. Nos. 4,867,149 and 5,188,123 to Falco and Gardner Jr., respectively, the entire contents of which are herein incorporated by reference.

Roll-down type earplugs are also lnown. Such earplugs simply comprise a compressible, resilient body portion made of a rubber, plastic, or, preferably, a foam material. The body portion is typically cylindrical or semi-cylindrical in shape and includes a circular cross-section having a diameter greater than that of the ear canal of a user. Insertion is accomplished by, first, compressing the body portion to a diameter less than that of the ear canal, second, pushing the body portion therein, and, third, allowing the same to decompress slightly to fill the ear canal, thus obstructing the ear canal and preventing passage of sound.

Such roll-down type earplugs may be found, for example, in U.S. Pat. No. 6,105,715 to Knauer, the entire contents of which are herein incorporated by reference.

Semi-aural devices comprise a curved band having first and second ends and a sound attenuating element disposed at each of said first and second ends. The curved band is generally composed of a rigid or semi-rigid plastic or rubber material while the sound attenuating elements are formed of a compressible resilient material such as a rubber, a plastic, or a foam-like material. The sound attenuating elements are generally inserted into the ear canal of the user by the push-in technique described above with reference to push-in type earplugs. When the sound attenuating elements are properly inserted into the ear canal, the curved band attaching the elements may be worn by the user as desired, for example, over the head, under the chin, behind the neck, etc. Such a semi-aural device is described, for example, in U.S. Pat. No. 4,461,290 to Gardner, the entire contents of which are herein incorporated by reference.

The described hearing protection devices have been designed and developed to provide a high degree of sound attenuation. Where a proper fit of the device is obtained, in many cases, nearly a complete attenuation of sound results. For example, roll-down type earplugs commercially available under the trademarks EAR Classic and EAR Ultrafit provide sound attenuation having a Single Number Rating (SNR) of approximately 28 dB and 32 dB, respectively.

Often, however, a lower sound attenuation is desired. That is, applications exist where a user desires sound to penetrate the hearing protection device and pass through the ear canal to the inner ear. In this way, a degree of hearing protection may be provided but the user is still permitted to hear sounds.

A hearing protection device with such characteristics is desired, for example, in moderately loud industrial settings where it behooves a user to hear workplace noises while still being provided with a level of hearing protection. For instance, a worker on a manufacturing floor may desire to hear voice communication from a colleague or sounds from a moving truck, etc. In such an instance, full or nearly full sound attenuation provided by many common earplugs is not desirable. Thus, a lower attenuating plug is needed.

Hearing devices, particularly earplugs, are known in the art which include provisions for reducing attenuating levels. See, for example, U.S. patent application Ser. No. 10/700,213 filed 03 Nov. 2003 entitled, "Low Sound Attenuating Hearing Protection Device", the contents of which are herein incorporated by reference in their entirety. The '213 application discloses a hearing protection device comprising a sound attenuating portion for insertion into the ear which includes a channel formed therethrough. The sound attenuating portion of the hearing protection device occludes the ear canal thus attenuating sound. The channel, on the other hand, allows sound to pass through the sound attenuating element and propagate to the inner ear of a wearer. The overall effect is a hearing protection device which provides a reduced sound attenuation. For example, the hearing protection device provides an SNR (single number rating) value of generally about 20. This is significantly reduced relative to the attenuation provided (about SNR 32) by the hearing protection device of the '213 application if produced without the channel.

It is often desired to maintain reduced attenuation throughout a broad frequency range such as from about 63-8000 Hz. Some previous attempts in this range have resulted in decreased attenuation at moderate and higher frequencies but, at lower frequencies, did not provide sufficient attenuation. Some hearing protection devices have been developed which can provide reduced attenuation over a broad range of frequencies but require expensive filters, damping elements, and/or electronic arrangements and are complicated to manufacture and assemble.

Accordingly, a hearing protection device is desired which consistently and effectively provides a low sound attenuation to a user's ear over a broad range of frequencies including lower frequencies and which is easy to manufacture, is cost efficient, and durable.

BRIEF SUMMARY OF THE INVENTION

The above discussed and other problems and deficiencies of the prior art are overcome or alleviated by the invention which provides A hearing protection device including a sound attenuating portion configured to be disposed within an ear canal of a user to obstruct a passage of sound, a channel formed through the sound attenuating portion configured to allow sound to pass through the sound attenuating portion when the portion is disposed within the ear canal, a tube disposed in the channel and configured to allow the sound in the channel to pass therethrough, and a filter disposed at one end of the tube and positioned at an interior of the sound attenuating portion, where the filter attenuates some of the sound passing through the tube.

The invention further provides a hearing protection device including a sound attenuating portion configured to be disposed within an ear canal of a user to obstruct a passage of sound, a channel formed through the sound attenuating portion generally along a longitudinal axis thereof wherein the channel is configured to allow sound to pass through the sound attenuating portion when the portion is disposed within the ear canal, a thin filter membrane disposed in the channel at an interior of the sound attenuating portion, where the filter includes a plurality of apertures which delimit areas of airflow resistance configured to attenuate the sound passing through the channel.

The invention also provides a method of manufacturing a hearing protection device. The method in one embodiment generally includes forming a sound attenuating element having opposing first and second ends, and forming a channel through the sound attenuating element from the first end to the second end, disposing a flexible filter membrane on a first open end of a tube such that side edges of the filter membrane extend beyond the diameter of the tube, inserting the filter membrane and the first end of the tube into the channel at the first end of the sound attenuating element, biasing the side edges of the filter toward a second opposing end of the tube and contacting the side edges of the filter with an outer surface of the tube, and pushing the tube into the channel such that the first end of the tube and the filter are fully disposed within the sound attenuating element and such that the side edges of the tube are disposed in a friction fit between the outer surface of the tube and a surface of the sound attenuating portion delimiting walls of the channel.

BRIEF DESCRIPTION OF THE DRAWINGS

Referring now to the drawings wherein like elements are numbered alike in the several figures:

FIG. 2A is a cross-section view of the earplug of FIG. 1;

DETAILED DESCRIPTION OF THE INVENTION

Figure 1:
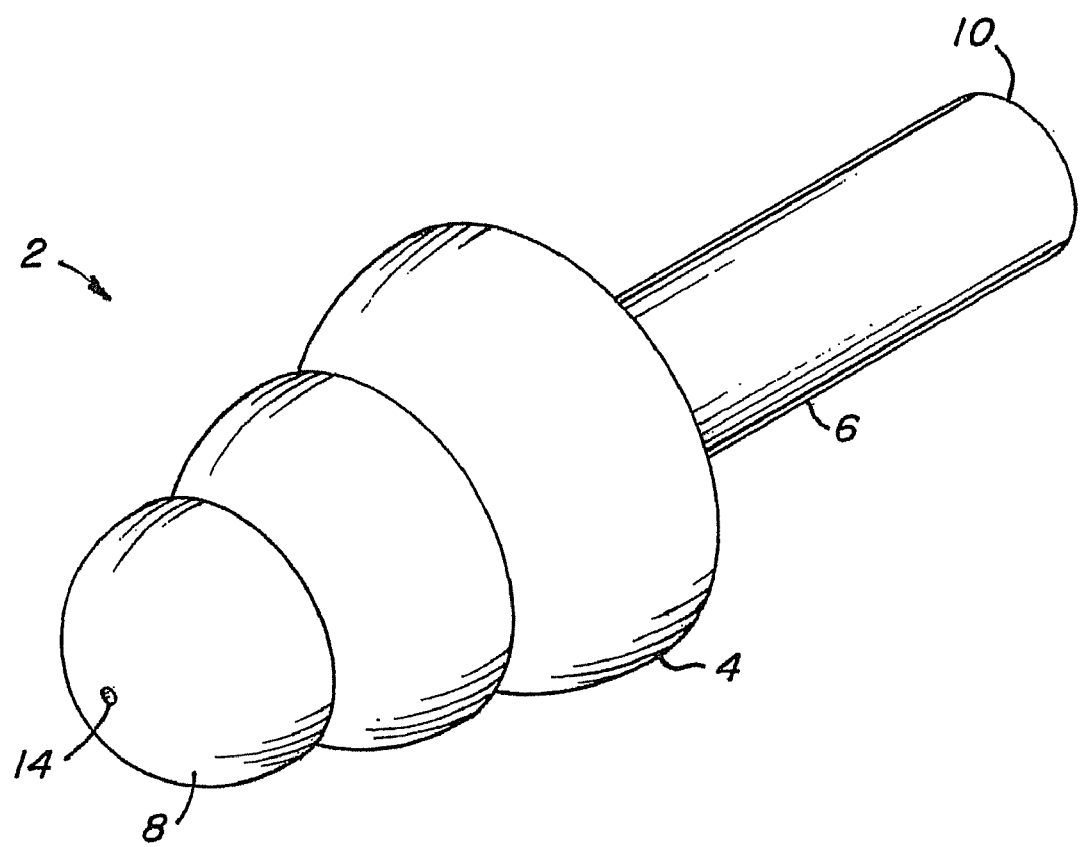
FIG. 1 is a perspective view of an earplug in one embodiment of the invention.
Figure 2B:
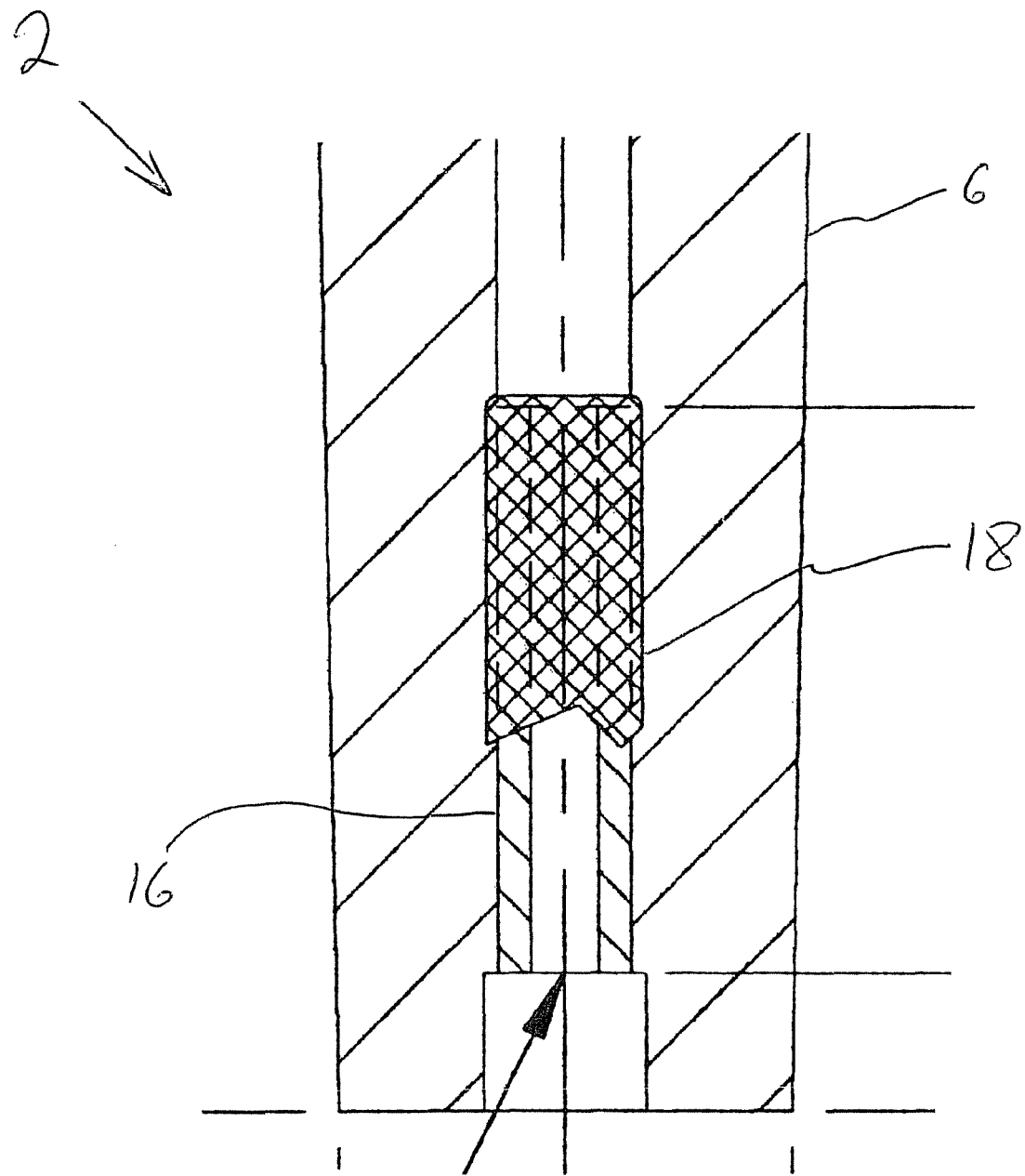
FIG. 2B is an enlarged partial view of FIG. 2A.
Figure 2C:
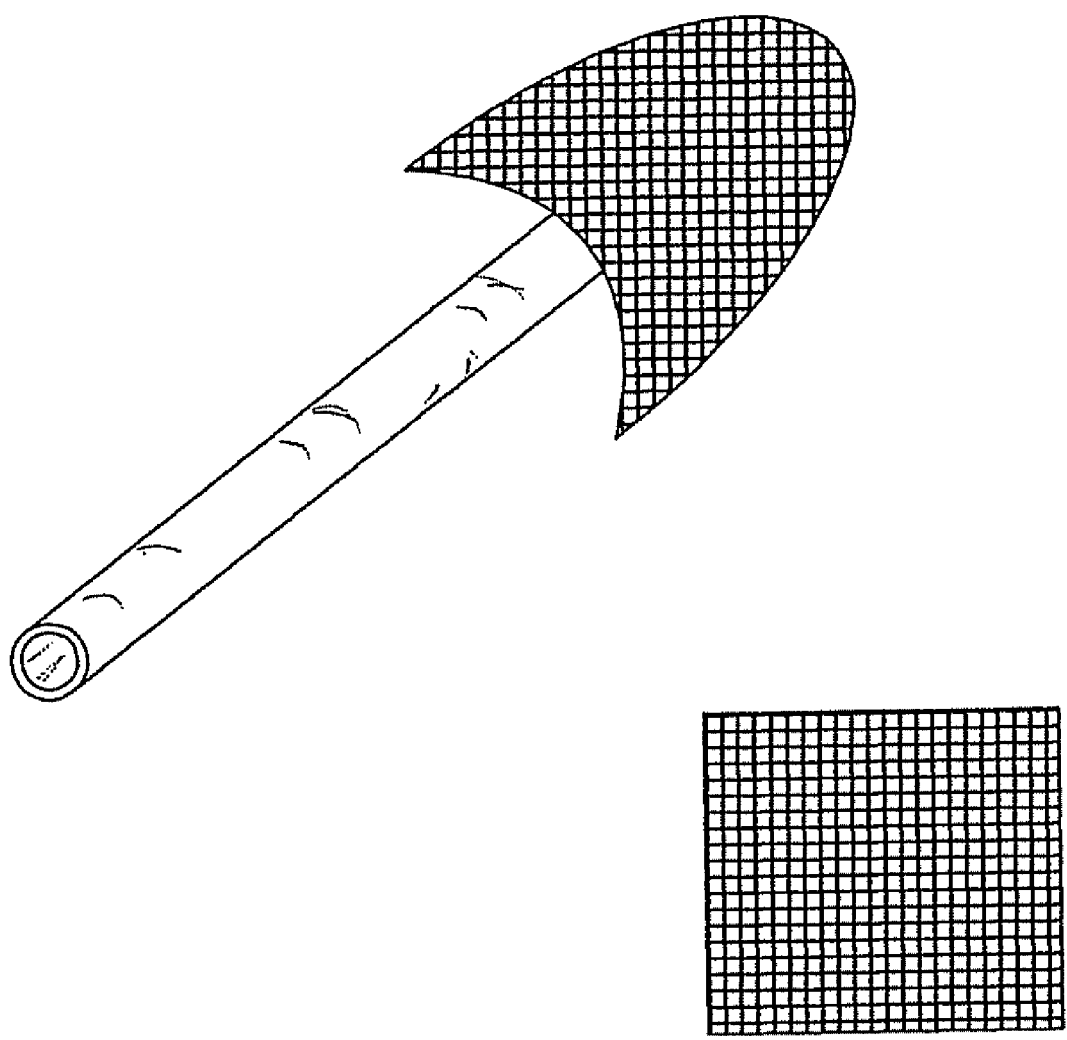
FIG. 2C is a view of a tube and a filter in an exemplary embodiment of the invention.
Figure 2D:
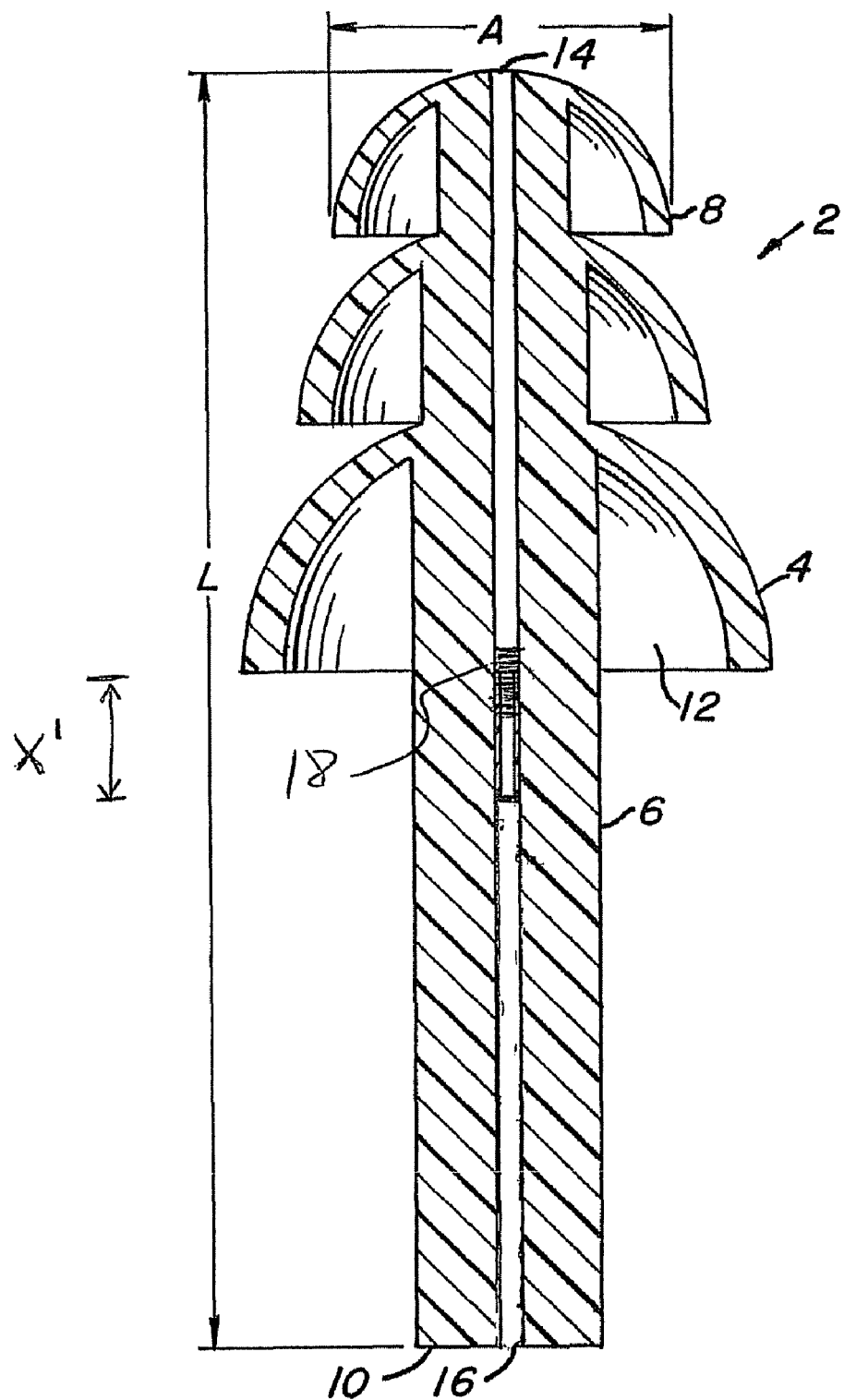
FIG. 2D is a cross-section view of the earplug of FIG. 1 in another embodiment of the invention.
Figure 3:
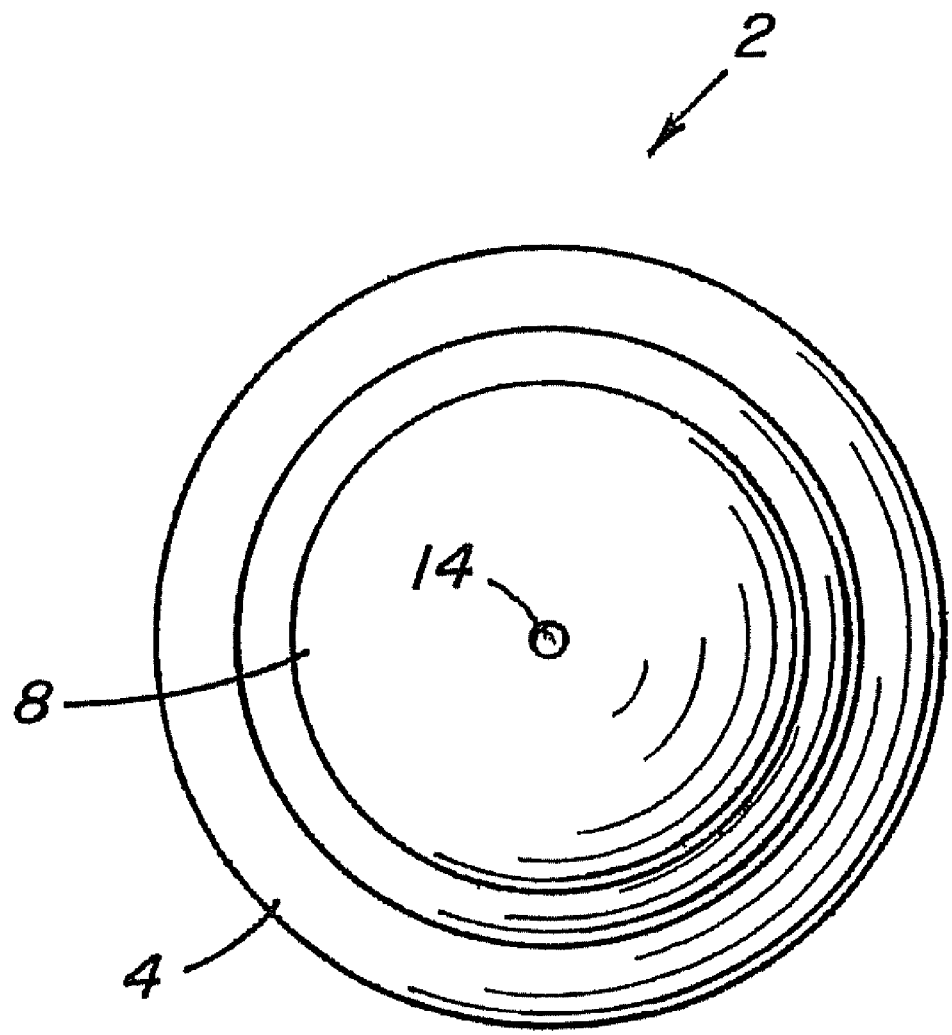
FIG. 3 is a front elevational view of the earplug of FIG. 1.

FIGS. 1-3 show a hearing protection device in one embodiment of the invention. Particularly, an earplug 2 is shown including flanges 4 emanating from an elongated stalk member 6. The stalk member 6 has a first end 8 from which a first of the flanges 4 emanates and an opposing second end 10 which extends longitudinally beyond the flanges 4. The flanges 4 are substantially hemispherical in shape and extend in a direction toward the second end 10 of the stalk member 6 such that spaces 12 are formed between a back side of the flanges 4 and the stalk member 6. Each of the plurality of flanges 4 includes a semi-substantially circular cross-section A. The flanges 4 are variously sized such that the cross-section A of the flange 4 proximate the first end 8 of the stalk member 6 is the smallest with each successive flange 4 having a larger cross-section A.

The stalk member 6 further includes a channel 14 formed therethrough along a longitudinal axis of the earplug 2. That is, the channel 14 extends through the stalk member 6 from the first end 8 to the second end 10. The channel opens to an exterior of the earplug 2 at the first and second ends 8, 10 of the stalk member 6. In a preferred embodiment, the channel 14 is substantially cylindrical in shape.

The earplug 2 further comprises a tube 16 disposed within the earplug 2 at the channel 14. That is, the tube 16 is fixed to the earplug 2, and more particularly, to an interior of the stalk member 6 at the channel 14. The tube 16 is hollow with a substantially cylindrical shape and may be positioned within the earplug 2 to extend from, be flush against, and/or recede into each of the first and second ends 8, 10 of the stalk member 6. In a preferred embodiment, as shown in FIG. 2A, the tube 16 includes one end set approximately flush against the second end 10 of the stalk member 6 and an opposing end disposed toward a middle of the stalk member 6 proximate the largest of the flanges 4.

The earplug 2 is generally composed of a resilient polymeric material and may be formed by any suitable conventional manufacturing techniques including, preferably, injection molding. The resilient polymeric material has a Shore A Durometer hardness value sufficient to provide the flanges 4 with a desired degree of pliability. The stalk member 6 may be formed of the material so as to possess higher hardness value thus providing a degree of rigidity to the earplug 2.

There are many known resilient polymeric materials which may be utilized effectively in the fabrication of the earplug 2 including, but not limited to, natural rubber, neoprene rubber, SBR rubber, silicone rubber, EPDM rubber, polybutadiene rubber, polyurethane elastomers, vinyl halide polymers, etc.

The tube 16 may be composed of any suitable material for providing the tube 16 with desired pliability, semi-rigidity, or rigidity. For example, the tube may be made of a polyetheretherketone (PEEK), a metal, a natural or synthetic rubber material, or a plastic material such as polyethylene, PVC, nylon, vinyl, etc., or combinations thereof.

The tube 16 is fixed to the interior of the stalk member 6 at the channel 14, preferably, by a friction fit. As mentioned, both the channel 14 and the tube 16 are substantially cylindrical in shape. The tube 16 includes an outer diameter $D_O$ and an inner diameter $D_I$. The outer diameter $D_O$ of the tube 16 is the diameter of the tube 16 measured from its outer surfaces, that is, those surfaces of the tube 16 which contact the earplug 2. The inner diameter $D_I$ of the tube 16 is the diameter of the tube measured from its inner surfaces, that is, those surfaces which do not contact the earplug 2. To provide the desired friction fit of the tube 16 within the channel 14, the outer diameter $D_O$ of the tube 16 is sized slightly larger than the diameter of the channel 14. Thus, when the tube 16 is inserted in the channel 14 the resilient polymeric material composing the portion of the stalk member 6 proximate the channel 14 is slightly displaced causing a compression/tension situation therein which creates the desired friction fit between the earplug 2 and the tube 16.

Alternatively, the tube 16 may be fixed to the earplug 2 at the channel 14 with a bonding agent. For example, a glue may be applied to the tube 16 and/or the channel 14 prior to the insertion of the former into the latter. Then, upon curing of the glue, the tube 16 is firmly bonded to the resilient polymeric material of the earplug 2.

As mentioned, the earplug 2 is formed by any suitable resilient polymeric material. The earplug 2 and/or parts thereof may be manufactured by any suitable process including, but not limited to, injection molding, casting, extrusion, etc.

The earplug 2 further includes a filter 18 disposed within the channel 14. In this exemplary embodiment, the filter 18 is disposed within the channel at one end of the tube 16. As shown in FIGS. 2A and 2B, the filter 18 is disposed upon and about an end of the tube 16 located in the channel 14 at the interior of the stalk member 6. Here, the filter 18 is a flexible porous membrane which wraps around and covers the interior end of the tube 16. In this illustrative example, the filter 18 is a mesh fabric, preferably a polyester, having approximately 400-500 threads per inch. The mesh fabric forming the filter 18 includes apertures each having a cross-sectional area of about $4 \times 10^{-7}$ square inches to about $6 \times 10^{-7}$ square inches and preferably about $4.9 \times 10^{-7}$ square inches.

The filter 18 is preferably secured upon the tube 16 and held within the channel 14 by a friction fit. Particularly, prior to inserting the tube 14 into the channel 16 as discussed generally above, the mesh filter is disposed at one end of the tube 16 and wrapped partially thereon. See, FIG. 2C. This end of the tube 16, with the mesh filter 18 thereon, is pressed into the opening of the channel 14 at the second end 10 of the stalk member 6 of the earplug 2. As the tube 16 is pushed into the stalk member 6, the interior end thereof and the mesh filter 18 disposed thereon travel through the channel until the position as shown in FIG. 2A is reached. As the tube 16 is pushed into the channel 14, the mesh filter 18 is forced tightly over the open end of the tube 16. Edges 19 of the filter 18 which extend beyond the outer diameter $D_O$ of the tube 16 are wedged between the tube 16 and the walls of the stalk member 6 delimiting the channel 14. This creates a tight friction fit of the filter 18 on the interior end of the tube 16, thus securing the filter 18 within the channel 14. Importantly, all of the edges 19 of the filter 18 extend beyond the outer diameter $D_O$ of the tube 16 such that there are no openings between the filter 18 and the inner diameter $D_I$ through which sound may pass unimpeded. That is, the filter 18 is secured on the tube 16 within the channel 14 such that, when the earplug 2 is inserted in a wearer's ear canal, all sound passing through the tube 16 and channel 14 must also pass through the filter 18.

In the current example, the mesh fabric filter 18 is substantially square shaped having a length and width of about 0.25 inches. Of course, this is merely illustrative. The filter 18 may be any shape having a dimension in one direction of about 3/16 inches and having a dimension in another substantially orthogonal direction of about 5/16 inches. More generally, the filter 18 comprises a size and a shape sufficient to entirely cover the inner end of the tube 16 and extend at least partially along outer sides of the tube 16 such that the tube 16 and filter 18 may be disposed within the channel 14 as discussed in the preceding paragraph. That is, the filter 18 may be square, rectangular, circular, oval, etc., or any combination thereof having the described dimensions.

In use, the second end 10 of the stalk member 6 acts as a handle which is gripped by a user during insertion. The earplug 2 is brought proximate the user's ear and then inserted into the ear canal. The first end 8 of the stalk member 6, and the smallest of the flanges 4 disposed there at, enters the ear canal first during insertion. Then, the earplug 2 is pushed into the canal by the second end 10 of the stalk member 6. The flanges 4 compress slightly during insertion and lodge in the ear canal to significantly block the passage of sound. A portion of the second end 10 of the stalk member 6 remains at the opening of the ear canal or slightly extending therefrom to act as a handle for removing the earplug 2.

The tube 16, as disposed in the stalk member 6, in combination with the channel 14, form a pathway through the earplug 2 such that, when the earplug 2 is properly inserted as described, a narrow column of air exists between the user's inner ear and the outer environment. This column of air essentially comprises a leak in the occlusion provided by the earplug and thus allows sound to penetrate the earplug and reach the auditory organs in the user's inner ear. In this way, a reduced attenuation is provided by the earplug such that, when properly inserted, the user hears sound from the outer environment but still is provided with a degree of hearing protection.

The column of air created by the channel 14 and the tube 16 is interrupted by the filter 18 extending across the interior end of the tube 16. The column of air is essentially an intended leak formed in the earplug 2 to allow sound to pass through the earplug 2 to the inner ear of a wearer. This leak reduces the overall degree of sound attenuation provided by the earplug 2. However, the apertures of the filter 18 form areas of airflow resistance which serve to attenuate or reduce an amplitude of a sound wave passing through the tube 16 to thus provide attenuation of some or all of the leaked sound. In this way, the filter 18 maintains the reduced attenuation provided by the channel 14 and tube 16, especially when the earplug 2 is subjected to low frequencies. For example, one test of the earplug 2 indicated an SNR of 14 when tested in accordance with Standard EN352-2.

The transmission of sound through the pathway created by the tube 16 is dependent upon, among other things, the volume of the column of air formed within the tube 16 and the porosity of the filter 18 covering the internal end of the tube 16. That is, at least the inner diameter $D_I$ and the length of the tube 16 (which delimit the internal column of air) and the filter aperture size and density (i.e., aperture per square inch) are critical parameters for the transmission of sound through the earplug 2.

Generally, the tube 16 may be of any outer diameter $D_O$ of sufficient size so as to be readily inserted into the channel 14 and so as to be held therein by a sufficient friction fit, as discussed above. The inner diameter $D_I$ of the tube 16 is chosen to facilitate a desired sound propagation. For example, the inner diameter $D_I$ is generally in the range of approximately 0.031 inch to approximately 0.062 inch. The corresponding length X of the tube 16 is approximately 0.200 inch to approximately 0.500 inch, respectively. More particularly, in one preferred embodiment, the inner diameter $D_I$ is approximately 0.030 inch and the length X is approximately 0.256 inch. In another embodiment, the inner diameter $D_I$ is approximately 0.020 inch and the length X is approximately 0.500 inch. As mentioned, the mesh fabric filter 18 is approximately 0.25 inches by 0.25 inches and includes apertures having an area of about $4 \times 10^{-7}$ to about $6 \times 10^{-7}$ in$^2$. The apertures are distributed evenly across the fabric filter 18 at a density of about 460 apertures per square inch.

An important feature of the earplug 2 is that the edges 19 of the filter 18 extend over and beyond the outer diameter $D_O$ limits of the tube 16 so as to wrap or cap the internal open end of the tube 16. That is, no open space is provided between the filter 18 and the inner diameter $D_I$ of the tube 16 through which sound could propagate unimpeded through the tube 16 and ultimately onto the inner ear of the wearer. This arrangement provides a low attenuation, but yet greater than zero attenuation, even at the lowest frequencies. For example, the earplug 2 can provide an SNR value of about 12 to about 17 when tested in accordance with Standard EN 352-2.

Compression or other deformation of the tube 16 during, for example, insertion of the earplug 2 into the ear canal of the user is clearly undesirable because such deformation of the tube 16 would result in corresponding deformation of the air column delimited thereby. Thus, the material(s) used to manufacture the tube 16 (see above) must be suitable to maintain the shape and dimensions thereof during ordinary use and handling of the earplug 2. For example, the tube 16 may be manufactured of a rigid or semi-rigid rubber or plastic material.

Additionally, the tube 16 in this embodiment is placed in the channel 14 proximate the second end 10 of the stalk member 6, as shown by example in FIG. 2A. This feature provides many advantages, including disposing the tube 16 so as to limit the compression forces exerted thereon when the earplug 2 is inserted into the earcanal. That is, during insertion, the flanges 4 are received within the earcanal and the second end 10 of the stalk 6 is positioned at the opening of the earcanal or extending therefrom. Thus, the flanges 4, not the second end 10 of the stalk member 6, receive the majority of compression forces associated with insertion of the earplug 2.

Additionally a comfort advantage is derived from disposing the tube 16 proximate the second end 10 of the stalk member 6. Particularly, the rigid or semi-rigid nature of the tube 16 does not effect a user while wearing the earplug 2 because, as mentioned above, the second end 10 of the stalk member does not generally lie within the earcanal when the earplug 2 is inserted. Thus, the user is only exposed to the comfortable, pliable nature of the first end 8 of the stalk member 6.

The portion of the channel 14 not buttressed by the tube 16 may be reinforced, as discussed herein, to counter the compressive forces of insertion. Alternatively, such channel may not include reinforcement and thus may compress slightly during insertion and/or use. However, the invention contemplates such condition and thus sizes the channel 14 appropriately such that compression of the channel 14 does not inhibit the desired passage of sound. That is, the pathway of sound or the 'leak' is maintained even during compression of the channel 14 due to the appropriately sized channel diameter.

Thus far, the tube 16 has been described illustratively as extending generally from the second rearward end 10 of the stalk member 6 to generally a middle of the stalk member 6 proximate the largest flange 4. See, FIG. 2A. However, the tube 16 may be of any desired length and may be disposed at any desired position within the channel 14. For example, as shown in FIG. 2D, the tube 16 has a length X' significantly less than that shown in FIG. 2A. Here, the tube 16 is disposed within the channel 14 at a position within the stalk member 6 away from the second end 10. The filter 18 is fitted on the end of the tube 16 most proximate to the first end 8 of the stalk member 6, as discussed above regarding the configuration of FIG. 2A.

Thus far, the invention has been described as including the tube 16 and filter 18 friction fit within the channel 14. However, the invention clearly contemplates other embodiments wherein, for example, there is no such tube 16. That is, in an alternate embodiment, the earplug 2 includes the channel 14 having appropriate inner dimensions to form the desired column of air extending through the earplug 2. In such embodiment, the filter is disposed within the stalk member 6 so as to extend entirely across the channel 14. For example, the filter may be bonded to the stalk member 6 at the channel 14 such that the filter 18 extends entirely across the channel 14. Alternatively, the filter 18 may be formed integrally with the stalk member 6.

The earplug 2, as shown and described herein, may further include a stem (not shown) embedded in and/or extending from the stalk member 6. The stem may be used: to provide a degree of rigidity to the stalk member; as a handle to facilitate insertion and removal of the earplug 2 from the ear canal of the user; to connect a cord or other device to the earplug; etc. The stem is disposed along the longitudinal axis of the earplug 2. Thus, the channel 14 extends through portions of the stalk member and through at least a portion of the stem. Such a stem is composed of a rigid or semi-rigid material such as a synthetic or natural rubber, a plastic, etc.

Figure 4:
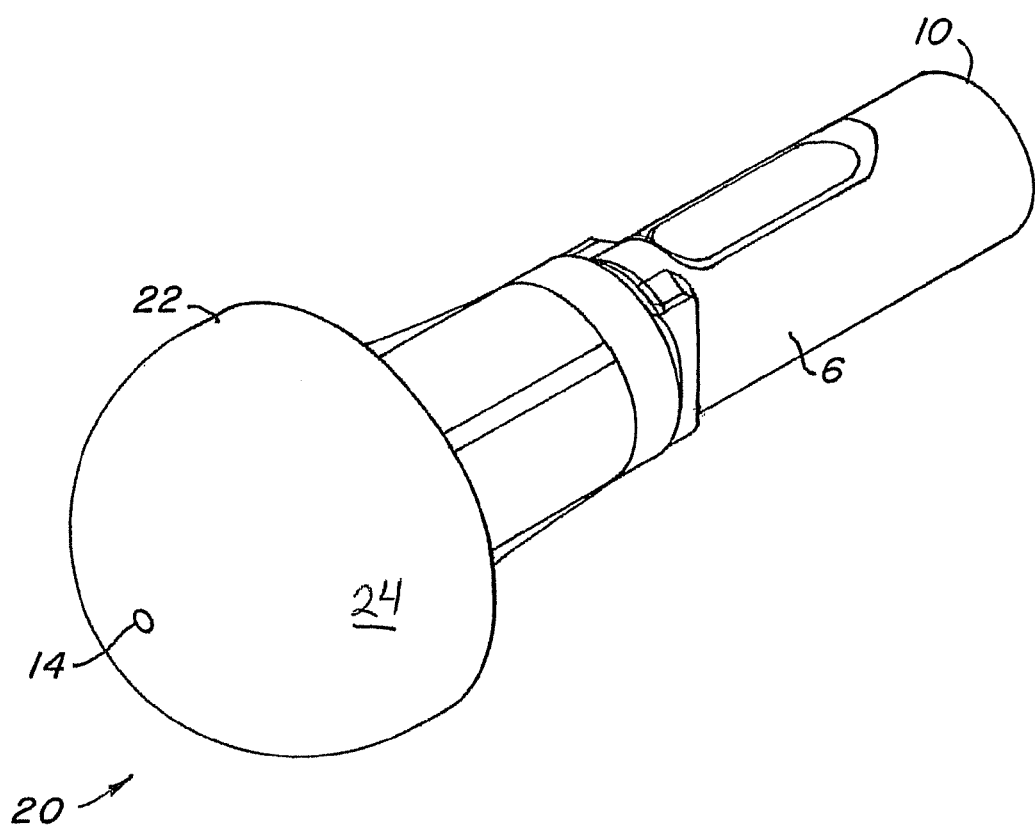
FIG. 4 is a perspective view of an earplug in a second embodiment of the invention.
Figure 5:
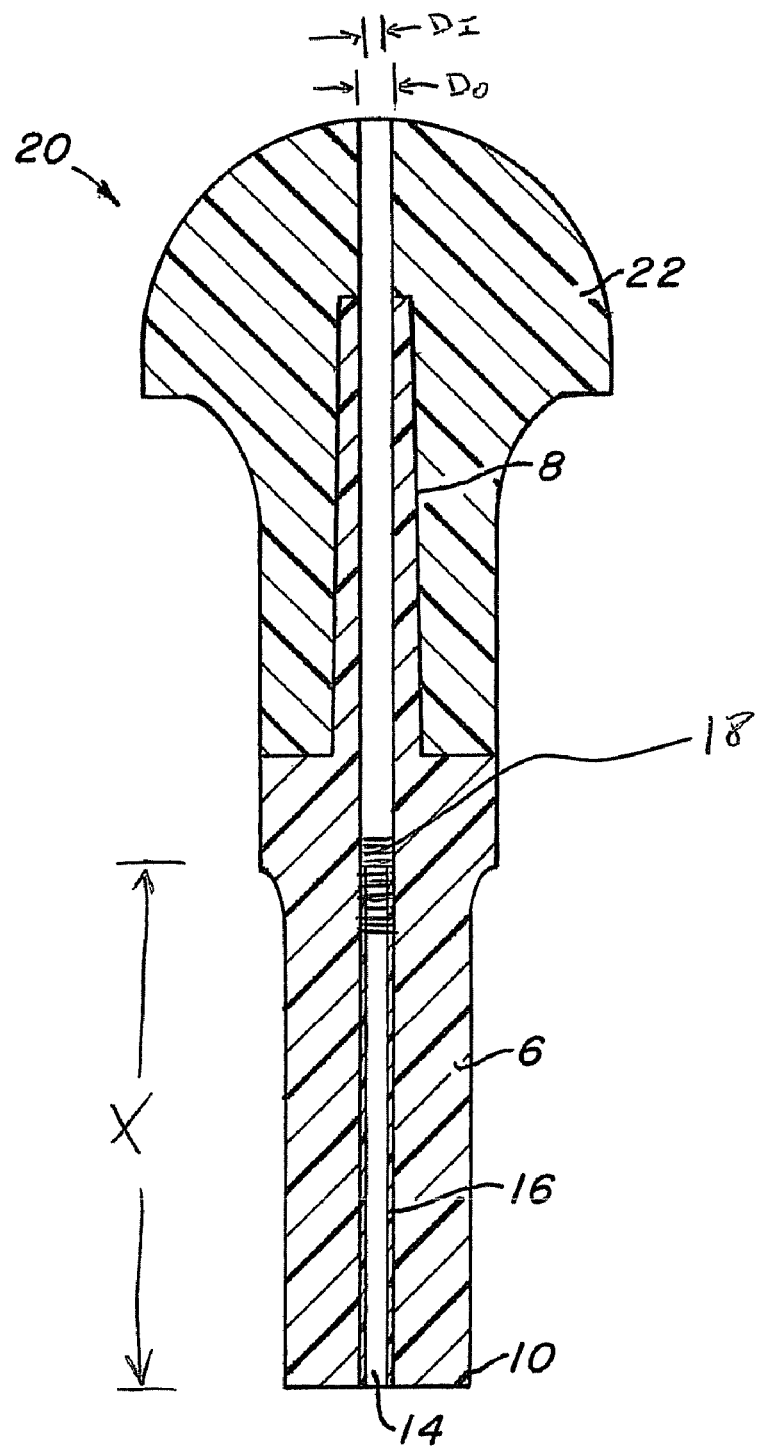
FIG. 5 is a cross-section view of the earplug of FIG. 4.

FIGS. 4-5 show an earplug 20 according to another embodiment of the invention. Please note, like parts and components are indicated herein and throughout with consistent reference numerals.

The earplug 20 includes a sound attenuating portion 22 disposed at the first end 8 of the elongated stalk member 6. The sound attenuating portion 22, generally, is any item which is insertable into the ear canal of a user and suitable for blocking and/or damping sound traveling through the ear canal. More specifically, as shown in FIGS. 4-5, the sound attenuating portion 22 is a substantially hemispherical lobe which extends rearwardly toward the second end 10 of the stalk member 6.

The earplug 20 further includes the channel 14 extending along a longitudinal axis of the earplug 20 through the stalk member 6 and through the sound attenuating element 22 such that the channel opens to the outer environment at an insertion surface 24 of the sound attenuating element 22 and at the second end 10 of the stalk member 6. The tube 16 is disposed within the earplug 20 at the channel 14 and held therein, preferably, by a friction fit which results due to the outer diameter $D_O$ of the tube 16 being slightly larger than the diameter of the channel 14. The tube 16 may extend the exact length of the channel 14 or may possess a length X less than or greater than the length of the channel 14. In a preferred embodiment, as shown in FIG. 5, the tube 16 is substantially shorter than the channel and is disposed proximate to the second end 10 of the stalk member 6. The filter 18 is disposed on the internal end of the tube 16 and extends completely across the inner and outer diameters $D_I$ and $D_O$ and wraps around sides of the tube 16 so as to be wedged between the tube 16 and the material of the stalk member 6 forming the channel 14. The disposition, features, and characteristics of the filter 18 relative to the earplug 20 are similar to those discussed above with regard to the earplug 2.

The stalk member 6, as mentioned above, is made of any suitable pliable, semi-rigid, or rigid material as is desired. Particularly, the stalk member 6 may be composed of a plastic or a rubber material and may be formed, preferably, by injection molding.

The sound attenuating portion 22 is made, preferably, of a compressible resilient material such as, for example, a compressible resilient plastic or rubber material or composition. Preferably, the sound attenuating portion is composed of a foam-like material composed of a soft, pliable self-rising foam with instant recovery properties such as a polyurethane or an acrylic blend foam. Other suitable foams include PVC, silicone, and nitrile, among others. A suitable foam is described, for example, in U.S. Pat. No. 5,792,998 to Gardner, Jr. et al., herein incorporated by reference. The earplug described therein is comprised of a dynamically stiff foam material having a low static stiffness, and a high dynamic stiffness. Another suitable foam is described, for example, in U.S. Pat. No. 4,158,087 to Wood, herein incorporated by reference. The sound attenuating portion 22 may be formed, for example, by a molding process and then bonded on the first end 8 of the stalk member 6 by a bonding agent such as a glue.

In use, the earplug 20 is handled by the second end 10 of the stalk member 6 and brought proximate the ear of a user. Then, the sound attenuating element 22 is inserted into the opening of the ear canal and inserted into the canal by pushing on the second end 10 of the stalk member 6. The sound attenuating element 22 compresses within in the ear canal and lodges therein to attenuate the passage of sound from the outer environment to the inner ear. The second end 10 of the stalk member 6 remains at or extends from the ear canal when the earplug 22 is full inserted. To remove the earplug 20, the user grasps the exposed second end 10 and pulls the earplug 20 from the ear canal.

As mentioned, the compressed sound attenuating portion 22 lodged in the ear canal provides attenuation, however, sound is permitted to reach the inner ear via the column of air formed and maintained by the channel 14 and the tube 16 extending through the earplug 20.

Here again, as described above with reference to FIGS. 1, 2, and 2A, the inner diameter $D_I$ of the tube 16 is approximately 0.031 inch to approximately 0.062 inch; the length X is approximately 0.200 inch to approximately 0.500 inch; and, more particularly, in one exemplary embodiment, the inner diameter $D_I$ is approximately 0.040 inch and the length X is approximately 0.256 inch, and in another embodiment $D_I$ is approximately 0.020 inch and L is approximately 0.500 inch.

The filter 18 of the earplug 20 includes apertures as discussed above which create areas of airflow resistance that attenuate or reduce the amplitude of a sound wave propagating through the tube 16 As discussed with respect to the earplug 2, the result of the earplug 20 is a reduced sound attenuation, greater than zero, across a range of frequencies including lower frequencies.

Additionally, while the earplug 20 has been described thus far as including the tube 16, the invention contemplates an embodiment of the earplug 20 without the tube 16 where the filter 18 is disposed and/or fixed within the channel 14 as discussed above with reference to the earplug 2.

Figure 6:
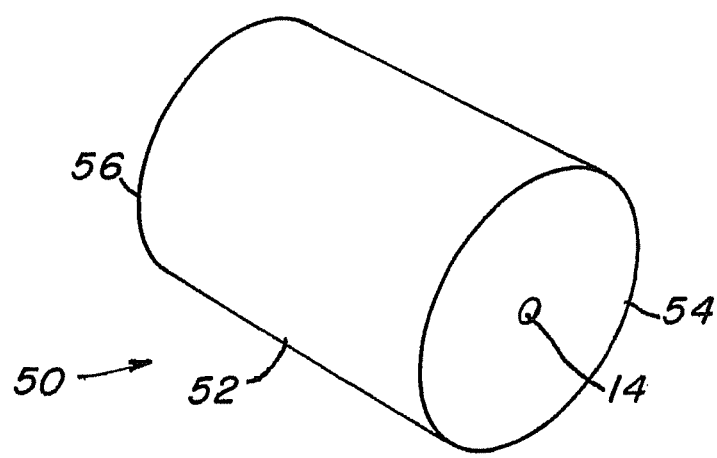
FIG. 6 is a perspective view of an earplug in third embodiment of the invention.
Figure 7:
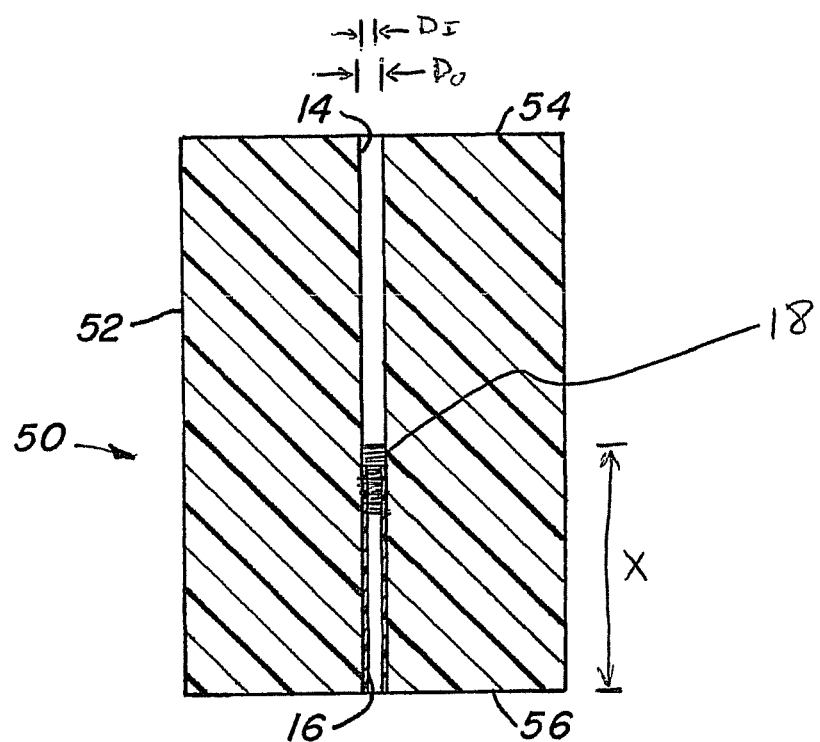
FIG. 7 is a cross-section view of the earplug of FIG. 6.

FIGS. 6 and 7 show an earplug 50 in another embodiment of the invention. The earplug 50 includes a body portion 52 having a first end 54 and an opposing second end 56. Additionally, the earplug 50 includes the channel 14 formed along a longitudinal axis thereof, from the first end 54 to the second end 56. The tube 16 is disposed within the channel and fixed therein to the body portion 52. The filter 18 is disposed on the internal end of the tube 16 and extends completely across the inner and outer diameters $D_I$ and $D_O$ and wraps around sides of the tube 16 so as to be wedged between the tube 16 and the material of the body portion 52 delimiting the channel 14. The disposition, features, and characteristics of the filter 18 relative to the earplug 20 are similar to those discussed above with regard to the earplug 2. The tube 16 and filter 18, as described previously, are preferably friction fit in the channel 14 but may be adhered or bonded as well.

The earplug 50 is formed of a compressible resilient material, such as, for example, a foam-like material. More particularly, the earplug 50 is composed preferably of a foam made of a polyurethane, an acrylic blend, a PVC, a silicone, a nitrile, etc. The earplug 50 may be formed by any suitable conventional manufacturing process including, but not limited to, molding, extrusion, die casting, etc.

The channel 14 may be formed at the time of manufacturing the body portion 52 or in a separate subsequent processing step. For example, where the body portion 52 is formed by molding, the pertinent mold includes an insert disposed therein which the body portion 52 forms about in order to form the channel 14. That is, the foam material, in a liquidous form, is injected into the mold. The insert is, for example, a pin shaped element extending within the mold. The foam material is allowed to expand and fill the mold around the insert. Once the foam is fully formed, the new body portion 52 is ejected from the mold. During ejection, the insert is removed from the body portion thus resulting in formation of the channel 14.

Alternatively, of course, the channel 14 may be made in a separate processing step. That is, the body portion 52 may be manufactured first and then the channel may be formed subsequently by, for example, drilling, etching, laser treatment as described in U.S. patent application Ser. No. 10/346,604 to Taylor herein incorporated by reference in its entirety, water jet treatment as described in U.S. patent application Ser. No. 10/660,015 to Schreiber herein incorporated by reference in its entirety, etc.

After formation of the body portion 52 and the channel 14, the tube 16 with the filter 18 thereon is inserted into the channel 14 and fixed therein to the body portion 52 in similar manner as that discussed with respect to the earplug 2. The tube 16 may have a length greater or less than a length of the channel 14. In the illustrated embodiment, the length of the tube 16 is substantially less than the length of the channel 14 and is disposed proximate the second end 56 of the earplug 50.

In use, the earplug 50 is first compressed to reduce a cross-sectional diameter thereof. Preferably, this is accomplished by the user rolling the earplug 52 between the fingers or hands about the longitudinal axis of the plug. This rolling/compression technique is applied until the diameter of the earplug 50 is approximately less than a diameter of the user's ear canal. Then, the first or second end 54, 56 of the earplug 50 is inserted through the opening of the ear canal and into the canal. The earplug 50 is inserted in the ear canal to a depth such that the trailing end 54, 56 of the body portion 52 is at or extending slightly from the opening of the ear canal. Once inserted into the ear canal, the resilient material composing the earplug 50 expands from its temporarily compressed state to fill the ear canal and lodge the earplug 50 therein, thus effectively attenuating the passage of sound.

However, while a significant degree of sound attenuation is achieved by the body portion 52 of the earplug 50, the channel 14 and tube 16 extending through the core of the body portion 52 delimits a column of air connecting the auditory organs of the inner ear to the outer environment. Thus, sound is permitted to travel from the outer environment through the tube 16 to the inner ear. In this way, the earplug 50 provides the user with a degree of hearing protection while still allowing sound to be heard, thus providing a relatively reduced attenuation.

The filter 18 is disposed within the earplug 50 such that some sound propagating through the tube 16 passes through the apertures of the filter 18. As mentioned previously, the apertures of the filter 18 delimit areas of airflow resistance which attenuate the leaked sound which passes through the tube 16. The inner diameter $D_I$ of the tube 16 of the earplug 50 is as described previously. The configuration of the earplug 60 results in a lowered attenuation (but a greater than zero attenuation) across a range of frequencies, especially including low frequencies.

As with other embodiments of the invention discussed herein, the earplug 50 has been described thus far as including the tube 16. Nonetheless, the invention clearly contemplates the earplug 50 as not including the tube 16. Such embodiment of the earplug 50 would include the channel 14 as described but shaped to have the particular dimensions discussed above with regard to the tube 16 in order to delimit the column of air as desired. In such embodiment, the filter 18 would be disposed and/or fixed within the body portion 52 of the earplug 50 at the channel 14 and extending there across so as to filter sound propagating through the channel 14 as discussed in detail above.

Furthermore, the earplug 50 is shown in FIGS. 6-7 having the tube 16 disposed in the channel 14 with one end abutting the second end 56 of the body portion 52 and with the other end of the tube 16 extending approximately midway through the body portion 52. This, of course, is an exemplary configuration. As with previous embodiments, the tube 16 may include a shorter length X than shown such that both ends of the tube 16 are disposed in the channel 14 in a central region of the body portion 52 of the earplug 50.

Hearing protection devices of the invention have thus far been described as including a single tube 16 disposed in a channel 14 extending through the hearing protection device where a single filter 18 is fitted on an interior end of the tube 16. This configuration is, of course, merely illustrative. A hearing protection device in accordance with the invention may include a plurality of tubes 16 disposed in the channel 14, each tube being fitted with a filter 18. For example, the earplug 2 of FIG. 2D may include a plurality of the small tube/filter arrangements 16/18 where such plurality is disposed along the length of the channel 14.

Figure 8:
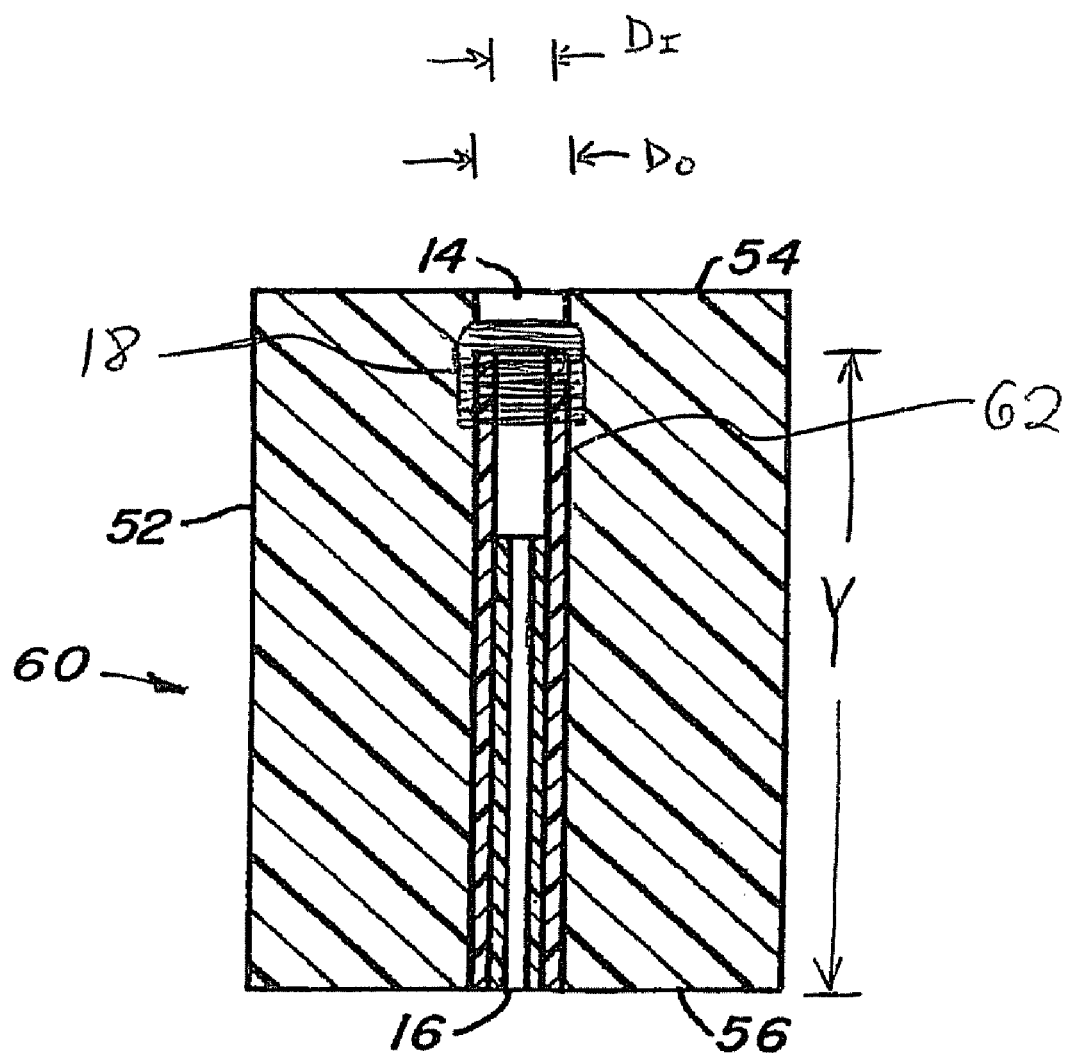
FIG. 8 is a cross-section view of the earplug of FIG. 6 in an another embodiment of the invention.

Further alternatively, in another exemplary embodiment of the invention, an earplug 60 is provided as shown in FIG. 8 including a channel 14 having a width slightly larger than in previous embodiments so as to receive and retain a second tube 62 within which the first tube 16 is disposed. The filter 18 is arranged as shown to cap and close an inner end of the second tube 62. The first tube 16 may be frictionally fit within the second tube 62 or alternatively may be bonded to the second tube 62 or formed integrally therewith, etc. A first end of the second tube 62 extends proximate to the first end 54 of the earplug 60. This first end of the second tube 62 is shown in FIG. 8 as extending beyond a first end of the first tube 16. Second ends of the first and second tubes 16, 62 are equally disposed generally flush with the second end 56 of the earplug 60. This configuration is, of course, exemplary and may be altered. For example, the first tube 16 may be more centrally located within the earplug body 52 such that the second tube 62 extends beyond both first and second ends of the first tube 16. It is also noted that the distance the second tube 62 extends beyond the first tube 16 at first and/or second ends may vary as desired and the second tube 62 may be positioned in the channel 14 so as not to abut either end 54, 56 of the earplug body portion 52.

As with the earplug 50 discussed above, the present earplug 60 provides a significant degree of sound attenuation but the first and second tubes 16, 62 extending through the core of the body portion 52, in combination with the remaining portion of the channel 14, delimit a column of air connecting the auditory organs of the inner ear to the outer environment when the earplug 60 is worn by a user. Thus, sound is permitted to travel from the outer environment through the tubes 16, 62 to the inner ear. Yet, as explained hereinabove, the filter 18 attenuates some of the sound propagating through this air column. In this way, the earplug 60 provides the user with a degree of hearing protection while still allowing sound to be heard, thus providing a low attenuation across a range of frequencies and especially at low frequencies.

The inner diameter $D_I$ of the first tube 16 is as described previously. The inner diameter $D_I$ of the second tube 62 is approximately 0.020 inch to approximately 0.090 inch; the length Y is approximately 0.100 inch to approximately 1.250 inches; and, more particularly, in a preferred embodiment, the inner diameter $D_I$ is approximately 0.062 inch and the length Y is approximately 0.700 inch. The channel 14 is sized correspondingly with respect to the first and second tubes 16, 62.

Figure 9:
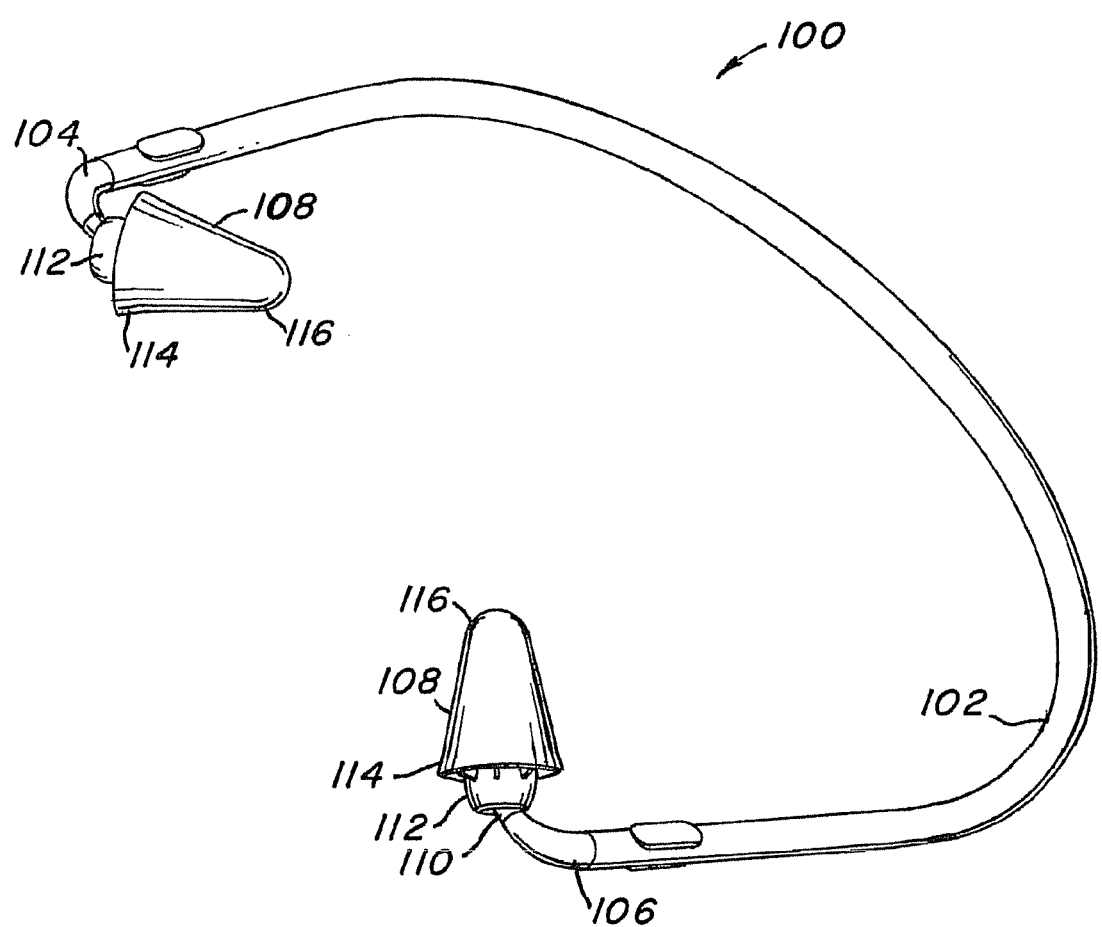
FIG. 9 is a perspective view of a semi-aural hearing protection device.
Figure 10:
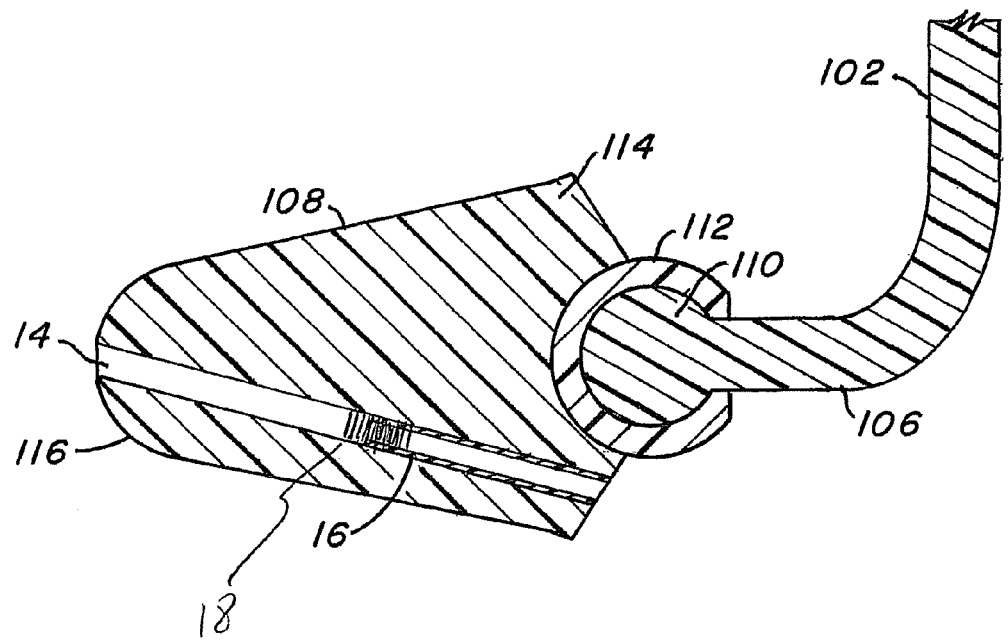
FIG. 10 is an enlarged cross-section view of a portion of the semi-aural device of FIG. 9.
Figure 11:
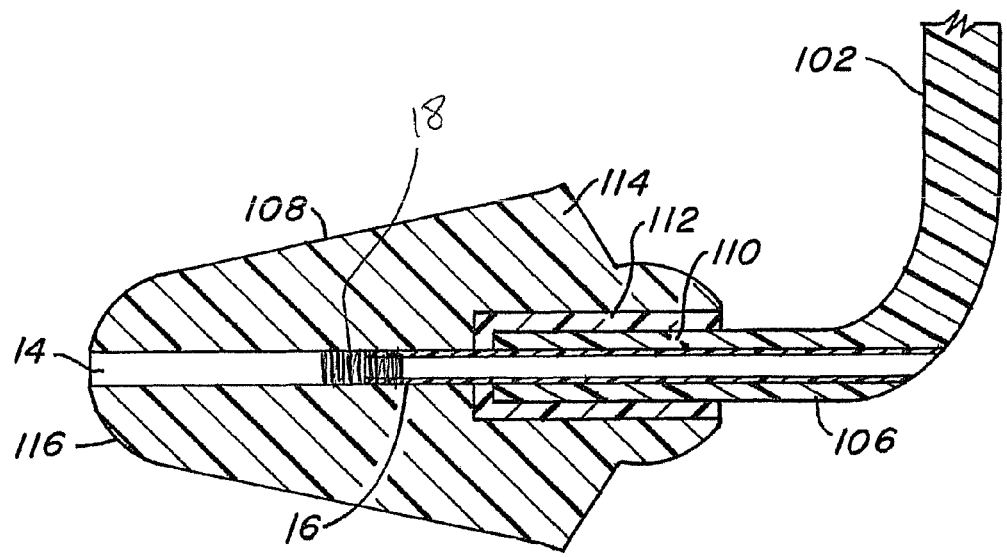
FIG. 11 is an enlarged cross-section view a portion of the semi-aural device of FIG. 10 in another embodiment of the invention.

FIGS. 9-11 show a semi-aural device 100 in one embodiment of the invention. The semi-aural device 100 includes a curved neck band 102 having a first end 104 and an opposing second end 106. Sound attenuating elements 108 are disposed at each of the first and second ends 104, 106 of the neck band 102. The neck band 102 includes a connection portion 110 disposed at each of the first and second ends 104, 106. The sound attenuating elements 108 each include a retention portion 112 which receives and retains the connection portion 110 of the neck band 102. The retention portion 112 is disposed at a distal end 114 of each sound attenuating portion 108. The distal end 114 is located opposite an insertion end 116 of the sound attenuating element 108.

In one embodiment, as shown in FIG. 10, the connection portion 110 of the neck band 102 is substantially spherical in shape. The retention portion 112 of the sound attenuating element 108 is correspondingly a hollow spherical form. Accordingly, the combination of the connection portion 110 and the retention portion 112 effectively forms a ball and socket joint which securely attaches the sound attenuating element 108 to the neck band 102 but allows the attenuating element 108 to pivot thereon.

In the embodiment, as shown in FIG. 10, the sound attenuating element 108 further includes the channel 14, the tube 16 fixed therein, and the filter 18 disposed upon and covering the inner end of the tube 16. The channel 14 may take any path from the insertion end 116 of the sound attenuating element to the distal end 114 and is show in an exemplary form as linearly traversing the element 108 at an angle to a longitudinal axis of the element 108.

In another embodiment of the semi-aural device 100, as shown in FIG. 11, the connection portion 110 is rod-like in shape and is received and fixably retained within the correspondingly shaped retention portion 112. Here, the connection portion 110 is fixed within the retention portion 112 by friction fit, bonding agent, etc. Thus, the sound attenuating element 108 is held rigidly to the neck band 102. The sound attenuating element 108 of this present embodiment further includes the channel 14, the tube 16 fixed therein, and the filter 18 disposed upon and covering the inner end of the tube 16. Here, the channel 14 extends linearly along a longitudinal axis of the sound attenuating element 108 from the insertion end 116 to the distal end 114 and through the retention portion 112, connection portion 110, and through the end 106 of the neck band 102.

Preferably, the sound attenuating elements 108 are formed of a compressible resilient material such as a rubber, a plastic, or a foam-like material. The neck band 102 is composed of a more rigid rubber or plastic material. The tube 16, as described previously, is composed of a rigid or semi-rigid material, such as a rubber or a plastic, in order to maintain the integrity thereof during handling and use of the semi-aural device 100. The tube 16 may extend through the entire described assembly or only through a portion or all of the sound attenuating element 108, as desired. Preferably, as shown in FIGS. 9 and 10, the tube 16 extends only partially into the 14 and is disposed proximate the distal end 114 of the sound attenuating element 108. The filter 18 is, for example, a mesh fabric square having apertures formed therethrough where the fabric square substantially wraps and covers the inner end of the tube 16 as discussed above with regard to previous exemplary embodiments of the invention.

In use, the insertion ends 116 of the sound attenuating elements 108 are brought proximate the ear canal opening of a user. The insertion ends 116 are passed through the ear canal opening and the sound attenuating elements 108 are correspondingly pushed into the ear canal wherein they are compressed and lodged into place, effectively attenuating sound. When the sound attenuating elements 108 are properly inserted, as described, the neck band 102 drapes beneath the chin or across the back of the neck or is placed over the head of the user to support the semi-aural device 100 and to facilitate handling thereof.

The tube 16 extending through the channel 14 of the sound attenuating elements 108 forms the column of air, discussed previously, connecting the inner ear of the user to the outer environment to allow sound to be heard by the user. Thus, the semi-aural device 100 provides attenuation to the user but still allows sounds to be heard, resulting in a low attenuation earplug. The filter 18, as discussed above, absorbs or dampens sound, particularly low frequency sound, propagating through the tube 16. The result is a semi-aural device 100 which provides a lower sound attenuation (but yet greater than zero) across a range of frequencies including lower frequencies.

The semi-aural device 100 has been described herein as including the tube 16. However, as discussed with reference to other embodiments of the invention, the semi-aural device may not include the tube 16 and may simply include the channel 14 sized and dimensioned appropriately to form the column of air through the sound attenuating elements for the propagation of sounds. Of course, in such embodiment, the filter 18 would either be fixed to the sound attenuating element 108 at the channel 14 or the filter 18 would be in a self supported friction fit within the channel 14.

While the channel 14 and the tube 16 have been shown and discussed herein and throughout as being generally cylindrical in shape and traversing a straight line path (for example, a longitudinal axis of the earplug as shown in FIGS. 2A, 5, 7, and 11), the invention clearly contemplates the tube 16 and/or the channel 14 as having any shape and traversing any path sufficient and suitable for creating a pathway for transmission of sound from the outer environment to the auditory organs of the inner ear of the user. For example, the tube 16 and/or the channel 14 may have any desired rectilinear and/or curvilinear cross-section and further may traverse and desired path through the particular hearing protection device (e.g., straight, angled, curved, helical, etc.). Additionally, the tube 16 and/or the channel 14 may have varying widths of cross-section along its length.

The earplugs shown and described herein and throughout may further include a stem and/or a cord extending therefrom. The stem and/or cord may be fixed to a surface of the earplug by a bonding agent or the stem and/or cord may be embedded partially in the earplug and thusly fixed thereto. The tube 16 and/or the channel 14 may extend through a portion of the stem and/or cord to complete formation of the column of air required to transmit sound to the inner ear of the user. In such case, the filter 18 would be disposed within the stem or cord. Alternatively, the tube 16 and/or the channel 14 may diverge from the point of connection of the stem and/or cord and vent at an end of the earplug opposite the insertion end.

The hearing protection device of the invention provides a device, particularly an earplug, which provides a user with a relatively low (but greater than zero) sound attenuation across a range of frequencies and especially at lower frequencies. The hearing protection device is of simple construction and only requires inexpensive tubing and filter. Furthermore, the earplug of the invention is easy to manufacture, is cost efficient, and is durable.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A hearing protection device, comprising:
a sound attenuating portion configured to be disposed within an ear canal of a user to obstruct a passage of sound;
a channel formed through the sound attenuating portion configured to allow sound to pass through the sound attenuating portion when the portion is disposed within the ear canal;
a tube disposed in the channel and configured to allow the sound in the channel to pass therethrough; and
a filter disposed at one end of the tube and positioned at an interior of the sound attenuating portion;
wherein the filter has a surface area greater than a cross-sectional area of the tube and attenuates some of the sound passing through the tube, and wherein the filter includes side edges that extend beyond an outer diameter of the tube and that are disposed in a friction fit between an outer surface of the tube and a surface of the sound attenuating portion delimiting the channel, such that the end of the tube is covered by the filter.

2. The hearing protection device of claim 1, wherein the filter comprises a membrane having a plurality of apertures formed therethrough.

3. The hearing protection device of claim 2, wherein the apertures each have a cross-sectional area of about $4 \times 10^{-7}$ square inches to about $6 \times 10^{-7}$ square inches.

4. The hearing protection device of claim 3, wherein the cross-sectional area is about $5.4 \times 10^{-7}$ square inches.

5. The hearing protection device of claim 1, wherein the sound attenuating portion includes a stalk member and at least one rearwardly extending flange disposed on the stalk member, wherein the channel extends through the stalk member generally along a longitudinal axis thereof, wherein the channel includes a length greater than a length of the tube, and wherein the end of the tube and the filter disposed thereon are positioned approximately midway along the length of the stalk member.

6. The hearing protection device of claim 5, further comprising a plurality of said rearwardly extending flanges, wherein each of said flanges is generally semi-hemispherical in shape and extends from the stalk member to delimit a space between the flange and the stalk member, wherein a first of said flanges is disposed at an insertion end of the stalk member, and wherein the remaining of said flanges are disposed along the stalk member and include serially increasing sizes in a direction away from the insertion end.

7. The hearing protection device of claim 1, wherein the sound attenuating portion comprises a generally cylindrical body portion formed of a compressible resilient foam which is configured to be compressed and inserted into the ear canal, and wherein the channel extends generally along a longitudinal axis of the cylindrical body portion.

8. The hearing protection device of claim 1, further comprising a band configured to extend around the head or neck or under the chin of the user, wherein the sound attenuating portion is disposed at an end of said band.

9. The hearing protection device of claim 8 wherein the channel extends through the sound attenuating portion and through a portion of the band.

10. The hearing protection device of claim 1, wherein the channel is substantially cylindrical and includes a diameter of at least approximately 0.040 inch and a length approximately equal to a length of the sound attenuating portion.

11. The hearing protection device of claim 10, wherein the tube includes an inner diameter of approximately 0.031 inch to approximately 0.062 inch and a length of approximately 0.200 inch to approximately 0.500 inch.

12. The hearing protection device of claim 11, wherein the inner diameter is approximately 0.040 inch and the length is approximately 0.250 inch.

13. The hearing protection device of claim 1, further comprising at least one of: a cord connecting the sound attenuating element to a second sound attenuating element; and a stem fixed to and extending from the sound attenuating element where the channel extends through at least a portion of the stem.

14. The hearing protection device of claim 1, wherein the tube comprises first and second tube portions, the first tube having a cross-sectional area greater than that of the second tube, the second tube being disposed at least partially within the first tube.

15. The hearing protection device of claim 14, wherein:
the first tube includes a length less than a length of the channel,
the second tube includes a length less than the length of the first tube,
the second tube is contained entirely within the first tube,
the first tube extends within the channel beyond the second tube, and
the filter is a flexible apertured membrane extending over the extended end of the first tube and wrapping around sides of the first tube so as to be disposed in a friction fit between an outer surface of the first tube and a surface of the sound attenuating portion delimiting the channel.

16. The hearing protection device of claim 15, wherein an inner diameter of the first tube is about 0.030 inch and an inner diameter of the second tube is about 0.060 inch.

17. A method of manufacturing a hearing protection device, comprising:
forming a sound attenuating element having opposing first and second ends;
forming a channel through the sound attenuating element from the first end to the second end;
disposing a flexible filter membrane on a first open end of a tube such that side edges of the filter membrane extend beyond the diameter of the tube;
inserting the filter membrane and the first end of the tube into the channel at the first end of the sound attenuating element;
biasing the side edges of the filter toward a second opposing end of the tube and contacting the side edges of the filter with an outer surface of the tube; and
pushing the tube into the channel such that the first end of the tube and the filter are fully disposed within the sound attenuating element and such that the side edges of the tube are disposed in a friction fit between the outer surface of the tube and a surface of the sound attenuating portion delimiting walls of the channel.

18. The method of claim 17 wherein said biasing of the filter side edges comprises pushing the tube in the channel toward the second end of the sound attenuating element such that the walls of the channel engage and fold the side edges in a direction toward the second end of the tube until the side edges contact the outer surface of the tube.

* * * * *